United States Patent [19]

Hager

[11] Patent Number: 4,495,793
[45] Date of Patent: Jan. 29, 1985

[54] SENSING DEVICE FOR DETECTING THE PRESENCE OF A GAS CONTAINED IN A MIXTURE THEREOF

[75] Inventor: Harold E. Hager, King County, Wash.

[73] Assignee: Washington Research Foundation, Seattle, Wash.

[21] Appl. No.: 412,840

[22] Filed: Aug. 30, 1982

[51] Int. Cl.³ .............................................. G01N 27/12
[52] U.S. Cl. ........................................................ 73/23
[58] Field of Search .............................. 73/23, 24, 643; 340/632, 633, 634; 250/370, 371, 358.1; 422/98

[56] References Cited

U.S. PATENT DOCUMENTS 3,276,004  9/1966  Maye .................................... 340/632
4,242,303 12/1980  Takahashi et al. ................... 340/634

OTHER PUBLICATIONS

"Chemisorption, Photodesorption and Conductivity Measurements on ZuO Surfaces", Y. Shapira et al., *Surface Science*, 54, pp. 43–59, 1976.

"A Model for the Operation of a Thin-Film $SnO_x$ Conductance-Modulation Carbon Monoxide Sensor", Henry Windischmann and Peter Mark, *J. Electro Chem. Soc.*, vol. 126, No. 4, pp. 627–633, Apr. 1979.

*Primary Examiner*—Stephen A. Kreitman
*Attorney, Agent, or Firm*—Seed and Berry

[57] ABSTRACT

A sensing device which senses the presence and/or concentration of one or more gases contained in a mixture is disclosed. An electrically charged semiconductor whose surface is in contact with the mixture of gases is illuminated with light, either intermittently or constantly. Changes in the transient and steady state conductivity of the semiconductor are measured and amplified. The form of the functionality between the gas and the conductivity changes is unique to a particular gas at a particular concentration and is used both to detect the presence and/or concentration of the gas.

15 Claims, 8 Drawing Figures

SENSING DEVICE FOR DETECTING THE PRESENCE OF A GAS CONTAINED IN A MIXTURE THEREOF

DESCRIPTION

TECHNICAL FIELD

This invention relates to a device and method of detecting the pressure and amounts of certain gases by employing the photo-impedance response dependence of a semiconductor sensor to the gas desired to be detected.

BACKGROUND ART

It has been known since the 1950s that the reversible chemisorption of reactive zones at the surfaces of certain metals, oxides and chalcogenides could be accompanied by reversible changes in conductance. This property has stimulated research and development in the use of semiconductor gas sensors for detecting the presence and amount of certain gases.

Growing concern for worker safety has stimulated development of research in this area for automatic toxic gas detection systems; however, the cost of available sensing systems is too high to justify widespread use. For example, automatic catalytic and electrochemical carbon monoxide detection systems are employed in mining and manufacturing facilities, but are too expensive for home use. There is a growing need for monitoring of carbon monoxide buildup in family residences, particularly new homes that are too airtight and where concentrations of toxic gases, such as carbon monoxide, can build up to dangerous levels. The utilization of semiconductor materials with impedance modulated by interaction with an adsorbed gas as a means of monitoring gas concentrations for carbon monoxide detection has required sensor temperatures maintained in the range of 300°–400° C. (570°–750° F.). This high temperature poses a safety hazard as well as requiring higher fabrication costs and energy use demands. At lower to moderate sensor temperatures, poor sensitivities result. The high sensor temperature requirement has been thought to be needed to achieve reversible carbon monoxide oxidation while, at the same time, maintaining high carbon monoxide sensitivity. Windischmann describes operation of a thin-film, tin oxide, conductance modulation carbon monoxide sensor in, "A Model for the Operation of a Thin-Film $SnO_x$ Conductance-Modulation Carbon Monoxide Sensor," *J. Electrochem Soc.*, Vol. 126, No. 4 (April 1979). Tests were performed with the semiconductor condenser heated to a temperature of from 200°–500° C. Outside of this range, the sensor ceased functioning. Within the temperature range of the sensor, the conductance of the sensor increased with the increase in the partial pressure of carbon monoxide in ambient gas.

The major design criteria for residential detectors for gases include (1) low cost, (2) automatic low maintenance, (3) safety, and (4) good sensitivity under a variety of background gas atmospheres.

DISCLOSURE OF INVENTION

It is a principal object of this invention to provide a device and system for detecting the presence of gases utilizing semiconductor materials by induced desorption/photo-excitation of the adsorbed gases.

It is a further object of this invention to provide a device for detecting gases utilizing an inexpensive sensing device which is supported by low power consumption and which can be operated at ambient temperature.

It is a further object of this invention to provide a device and system which includes means for measuring the transient and steady state conductivity change of an electrically charged semiconductor whose surface is in contact with the gases whose presence and/or concentration is desired to be detected, the semiconductor surface illuminated with light intermittently or constantly.

What is described in this application is a sensing device which utilizes a semiconductive film sensor surface which is exposed to the gases to be detected and/or measured. The impedance of the semiconductive film is capable of modulation by chemisorption of the gas molecules of one or more of the gases in contact with the film surface. An electrical potential is established across the surface of the semiconductive film. The film surface is illuminated with light of sufficient frequency and intensity to cause photodesorption of gas in the gas mixture being measured. Means are used for amplifying and measuring the transient and steady state change in conductivity of the semiconductor film as a measure of the presence and/or concentration of the gas being chemisorbed.

BEST MODE FOR CARRYING OUT THE INVENTION

Figure 1:
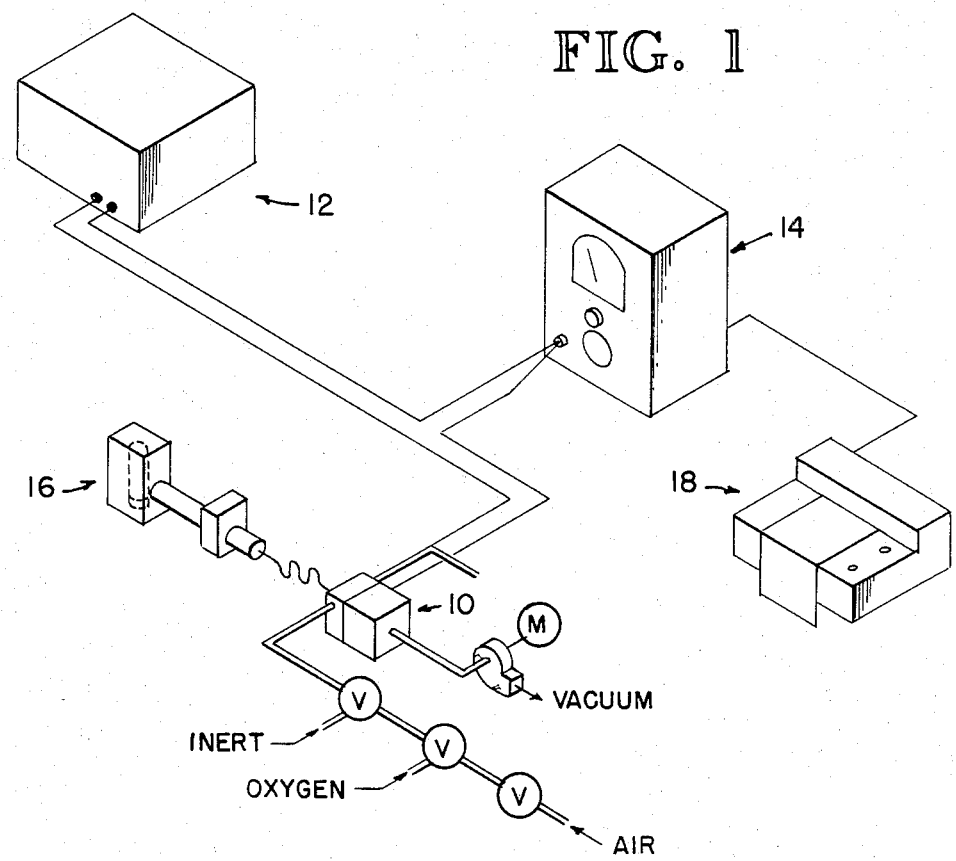
FIG. 1 is a schematic of an apparatus employed for detecting photo-induced current response to various semiconductive films.

The semiconductive material is coated as a thin film on suitable substrate materials. The semiconductive materials which may be used include certain metal compounds, metal oxides (such as $SnO_2$, $THO_2$, $Fe_2O_3$, $ZnO$, $Cu_2$), and chalcogenides. Generally, these materials are compound semiconductors with band gap energies ranging from 0.5 eV to 5.0 eV. In the case of the metal oxides, they may be either the pure oxide or the oxide doped with suitable noble metals, such as ruthenium, palladium, rhodium, etc. The thin-film oxide coating may be prepared by several methods. Thermal fabrication is a convenient method for growing thin films. A solution of metal oxide particulates or metal chlorides of the metal desired is prepared in the desired stoichiometries and a layer sprayed onto a suitable substrate, such as a porous porcelain plate. The substrate with the coating of metal oxide or chloride is then placed on a support stand and put in an oven at a temperature ranging from 550°–650° C. After achieving thermal equilibrium, further layers of film are applied over the initial layer at a film deposition rate of about 0.2 microns/minute. After 3–5 hours of heating, the samples are retrieved and cooled to room temperature. A film thickness in the range of 1–20 microns is suitable.

The semiconductive coating should have the ability to chemisorb gas molecules on its surface and preferably has a wide bandgap. For carbon monoxide detection, the semiconductive coating should maintain high carbon monoxide sensitivity, achieve photoexcitation of carbon monoxide removal and have a resistivity of at least $10^4$ ohms/inch and preferably at least $10^7$ ohms/inch.

The semiconductive surface is illuminated, preferably perpendicular to the semiconductor surface, with a scan of light which alters the population distribution of the semiconductor surface states. The illumination, if sub-bandgap irradiation levels are involved, excites holes from the valence band to some semi-discrete energy level at which photooxidation occurs. To conserve energy, the illumination is preferably pulsed at the semiconductive surface at the appropriate wavelength for affecting the surface state of the semiconductor. For carbon monoxide detection, the semiconductive surface is subjected to energy greater than the bandgap energy $h\gamma=2.0–3.4$ electron volts at an intensity of 90 to 350 microwatts/$cm^2$ at a frequency ranging from 380 to 680 nm.

An electrical potential is established across the semiconductive film by connection to a source of electrical energy. Conductivity changes in the film are proportional to the photocurrent change response, which is dependent on the type and amount of gas in contact with the semiconductive film. The change in conductivity of the semiconductive film can be amplified or otherwise modified by the use of appropriate amplification means, such as a solid-state RAM chip. The current or conductivity change of the semiconductor over a period of time, when the surface of the semiconductor is exposed to a particular gas at a particular concentration and the surface is subjected to light and/or dark conditions, produces transient and steady state conductivity changes unique to that particular gas at that concentration. The electronics of the device can be made to detect certain conductivity state changes unique to one or more gases at certain concentrations. For example, a system can be adjusted to sound an alarm if the concentration level of a particular gas in contact with the semiconductor surface reaches a certain threshold level.

The variables which should be considered in constructing a detector for sensing various gases include (1) thickness, composition and structure of the semiconductive film, (2) illumination intensity, (3) illumination frequency, (4) the dopant, if any, used with the semiconductive film and the dopant level, (5) the gas concentration being measured, (6) the conductivity of the semiconductive film, and (7) the time interval of illumination and nonillumination when pulsing is used.

FIG. 1 illustrates a prototype apparatus for measuring and recording transient photocurrent change responses for selected semiconductive sample surfaces. A sensor cell 10 made from insulating Plexiglas to maintain the semiconductive film at room temperature and reduce stray noise holds the semiconductive film. Copper cladding, spaced one centimeter apart on the film surface, connects the thin film to the circuit. Spring pressure applied by a brass plunger holds the film with a constant force against the metal contacts. The sensor employs a face plate designed for fast gas changes. The semiconductive film is connected to a variable voltage source 12 and to an electrometer 14, such as a Keithley Instrument solid-state electrometer. Changes in conductivity are recorded by a recorder 18. The exposed face of the semiconductor surface faces a source of light. Means for introducing the various gases into contact with the face of the semiconductive surface are included. The semiconductive surface is illuminated by a suitable light source 16 whose visible light output passes through a monochromator or filter for screening out all but certain wavelengths of light. The light, after passing through the monochromator, strikes the semiconductive surface. A desired potential, such as 10 volts, is placed across the semiconductive surface and used as the test potential.

EXAMPLE 1

Semiconductive films prepared for testing in the apparatus of FIG. 1 included $TiO_2$, $SnO_2$ and ZnO. In each instance, an electrically insulating substrate was cut to the rectangular shape required to get within the cell. A three millimeter thick slab of porous porcelain (Sargent Welch Company Catalog No. 128) was commonly used as the substrate piece, cut in a rectangular shape to give about 1.67 $cm^2$ of surface area. This total specimen area allows for approximately 1 $cm^2$ of the metal oxide to be exposed to the ambient atmosphere. The latter area was convenient in the prototype study, facilitating direct reporting on the basis of per square cm of exposed surface.

The thin films applied to the porcelain substrate were oxidized using the thermal fabrication technique as described previously. Solutions of metal oxide particulates or metal chlorides were prepared in the desired stoichiometries and sprayed onto the porcelain surfaces using an Airkem air brush atomizer. Spraying was carried out at a pressure of 20 psi using pure oxygen as the carrier gas. Prior to deposition of the film, the porous porcelain samples to be sprayed were placed on a 0.25-inch mild steel support stand and placed in an oven at a temperature of 600° C. After thermal equilibrium was achieved, the solutions were sprayed at a rate to maintain a deposition rate of about 0.2 microns/minute. After deposition of the metal chloride or oxide on the surface, the temperature to which the porcelain plate was subjected was increased to above that necessary for complete conversion of any lower oxidation states. After 3–5 hours, the samples were retrieved and cooled to room temperature.

By accurately weighing samples before and after the spray treatment, a fair estimate of film thickness was calculated. The films prepared had thicknesses ranging from about 1–20 microns.

Semiconductive films prepared in this manner were placed in the cell of FIG. 1 between copper contacts which connected them to the bias and measurement circuits. Photoinduced current changes were measured by illumination of the semiconductive surface perpendicular to the plane of the diagram. A visible light source (pulsed or not pulsed) having wavelengths ranging from 400–700 nm is an inexpensive, low-power consumption source of illumination of the metal oxides tested. The illumination used consisted of bandgap or subbandgap energy. A light-emitting diode may be employed as the light source. The width of the semiconductor bandgaps generally determines the amount of energy needed to excite a valence band electron to an energy level in the conduction band.

Spectral scans were initiated at a monochromator scanning rate of 8.4 nm/min. During the spectral scans, the metal oxide films were subjected to an oxygen atmosphere. Current changes generated by photoexcitation of surface states gave a rough measure of photo-induced changes in the surface state distribution. Table 1 illustrates the spectral response characteristics of the metal oxide films.

TABLE 1

Spectral Response Characteristics of Metal Oxides

| Oxide | Gap Width, eV | PC Response | Peak Wvlgth, nm |
|---|---|---|---|
| SnO$_2$ | 3.2 | Yes | 573, 390 |
| TiO$_2$ | 3.2 | Yes | 540, 390 |
| ZnO | 3.3 | Yes | 625, 380 |

Using the apparatus illustrated in FIG. 1, experiments were performed to determine photocurrent change response to different carbon monoxide concentrations at various wavelengths of light using zinc oxide and zinc oxide doped with palladium, ruthenium and rhodium. An assay of the zinc oxide powder used in preparation of the semiconductive film showed the following analysis:

Insolubles in H$_2$SO$_4$:0.005%
Chloride:0.0003%
Nitrate:0.003%
Sulfur Compounds:0.003%
Arsenic:0.0001%
Iron:0.004%
Lead:0.003%
Manganese:0.0005%
Substances Not Precipitated by (NH$_4$)$_2$S:0.110%
Water (presumed):0.7%

The zinc oxide samples doped with the noble metals were prepared by spraying one ml of 0.01 M metal chloride aqueous solutions (PdCl$_2$, RuCl$_3$ and RhCl$_3$) mixed with 5 ml water onto the zinc oxide films at 600° C. To ensure oxidation of the dopants, the temperature to which the films were subjected was increased to 850° C. and the films maintained in the oven for two hours. Initially, the semiconductive zinc oxide films were contained in a dark state prior to illumination. Referring to Table 2, the peak response magnitudes are relative changes in current across the high-resistance zinc oxide film when illuminated with the corresponding wavelength of light in an oxygen atmosphere.

TABLE 2

Comparative Photocurrent Response Peaks for Several Different ZnO Films

| Film | DC × 10$^7$ amps ± 2% FS | Pk Wvlgh, nm | PM × 10$^7$ amps ± 5% FS |
|---|---|---|---|
| Plain | 4.0 | 665, 625 380 | 11.0, 12.0 53.0 |
| Pd doped | 0.4 | 665, 380 | 1.52, 33.5 |
| Ru doped | 3.1 | 680, 635 560, 380 | 1.45, 1.45 0.45, 92.0 |
| Rh doped | 0.3 | 535, 380 | 0.35, 30.0 |

Positive carbon monoxide responses were also recorded for some of the above wavelengths. The data in Table 2 defines the wavelengths needed to excite semi-discrete electronic energy levels of ionized oxygen so that a change of conduction results. The amplitude of photocurrent change response increased as applied surface illumination intensity was increased from 450–380 nm. Other peaks in Table 2 indicate evidence of existing surface state levels present because of the intrinsic surface states, noble metal dopants used and impurities contained in the zinc oxide material from which the semiconductive films were made.

EXAMPLE 2

Table 3 illustrates results for the palladium-doped zinc oxide semiconductive film exposed to constant illumination and to carbon monoxide at various times of illumination when photoexcitation was occurring. The rate of photocurrent change is expressed as:

$$d(\Delta i)/dt \times 10^7 \text{ amps/min} \pm 9\% \text{ FS.}$$

TABLE 3

Initial Rate Comparison of Photocurrent Change at Longer Wavelengths

| Surface | Wvlgh, nm | d(Δi)/dt × 10$^7$ amps/min ± 9% FS |
|---|---|---|
| Plain | 625 | 2.86 |
| Pd doped | 680 | 0.19 |
| Ru doped | 635 | 4.36 |
| Rh doped | 535 | 2.19 |

Figure 2:
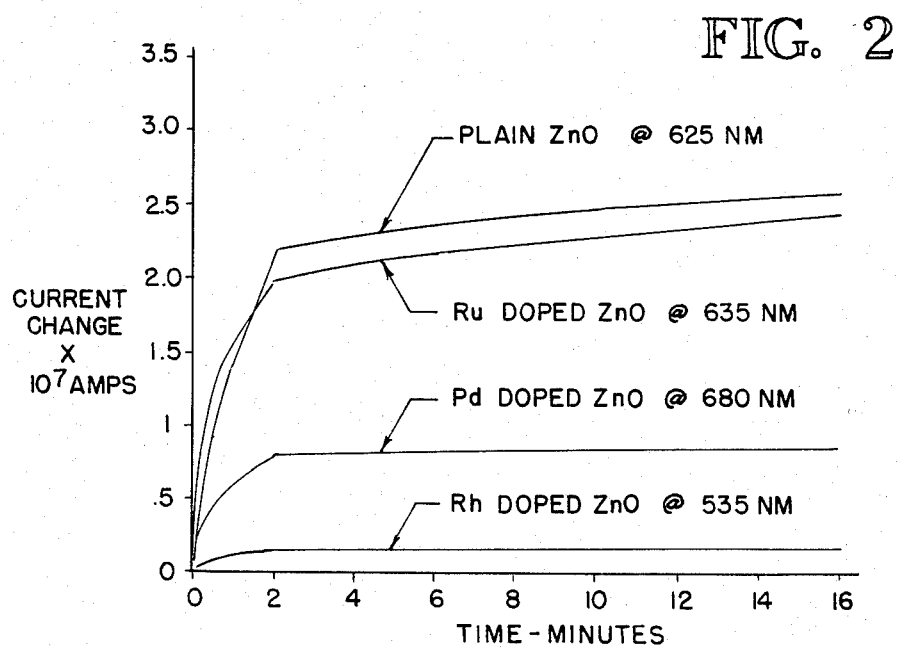
FIG. 2 is a graph of the current-time response relationship for various ZnO films exposed to a 50% carbon monoxide atmosphere at constant illumination.

FIG. 2 provides a brief summary of the results obtained with the various semiconductive films at longer wavelengths. The time response characteristics were also measured at lower CO concentrations and were found to be similar in form and timescale to the curves of FIG. 2.

Figure 3:
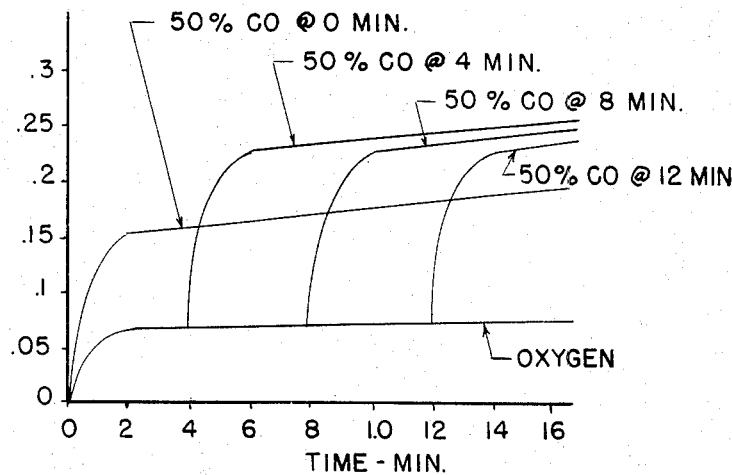
FIG. 3 is a graph of the current time response relationship for Pd doped ZnO exposed to 50 percent CO Mixture Injections at constant illumination.
Figure 4:
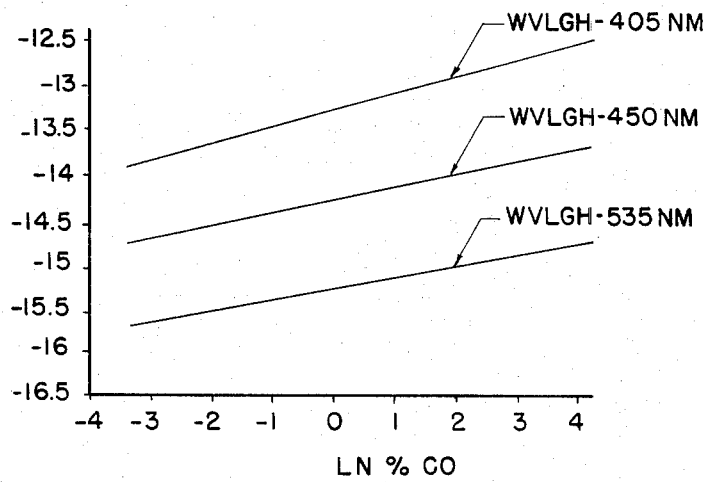
FIGS. 4 to 7 are graphs of the rate of the current change-concentration relationship for Rh-doped ZnO films, Pd-doped ZnO films, Ru-doped ZnO films and plain ZnO films.
Figure 5:
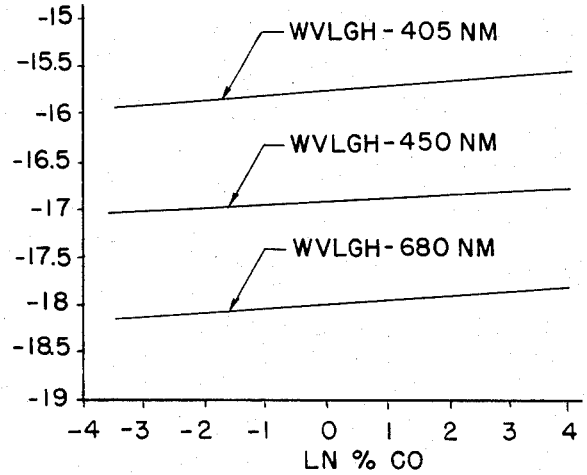
Figure 6:
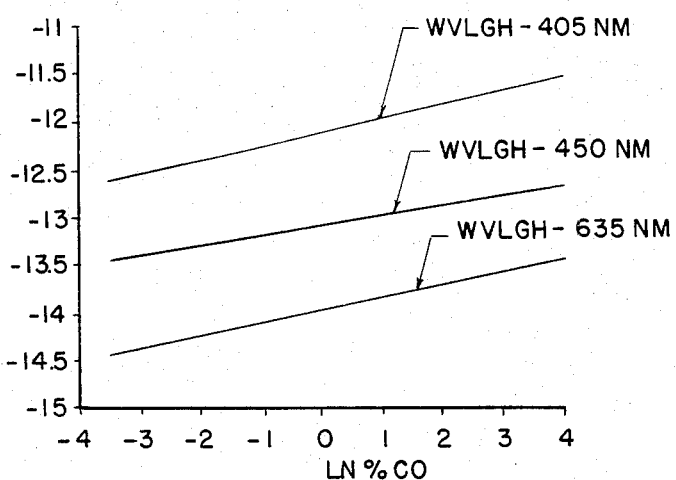
Figure 7:
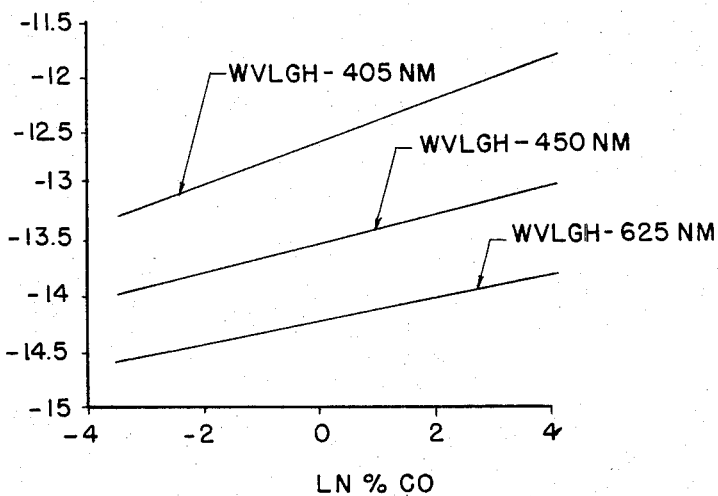

FIG. 3 shows an example of results for Pd doped ZnO exposed to CO at various times of illumination when photo-excitation was occurring. Photocurrent response to 50% CO mixtures appears to be independent of injection timing both in terms of curve form and magnitude of response. As suggested by trials performed for different surfaces at longer wavelengths, the rate of change of current to CO exposure is relatively constant.

A practical sensor probe for carbon monoxide or other gases is required to quickly detect concentrations of carbon monoxide and distinguish these signals from those of other background constituents, such as other oxidizable gases. Both sensitivity and the rate of photocurrent change characterize detector performance. Sensitivity, s, is defined by the following equation:

$$s = (\Delta i_{co} - \Delta i_{o2})/i_{is}$$

where $\Delta i_{co}$ equals the photoresponse current change of the film when in contact with the test environment, $\Delta i_{o2}$ equals equals the photoresponse current change of the film when in contact with an oxygen atmosphere, and $i_{is}$ equals the dark current value of the particular film being used.

EXAMPLE 3

Characterization of a sensor can also be achieved by noting dependence of rates of current changes with concentration either in the dark or light state. As with sensitivity measurements, this data provides a clue to the essence of surface state processes. The functionalities obtained from the assorted data fit a power law dependence fairly well. Scatter was much more evident for the rate of current changes-concentration data than sensitivity-concentration data. FIGS. 4 to 7 relate this power law dependence for the four different ZnO surfaces in question over the concentration range from 0.04% to 50% CO in O$_2$. The dependence of both sensitivity and rate of current change with concentration are tabulated in Table 4 and graphed in FIGS. 4 to 7 as slopes of each line.

TABLE 4

Slopes of Sensitivity and Rate of Current Change Curves

| Surface | Wvlgh, nm | S Slopes | Rate Slopes |
|---|---|---|---|
| Plain | 625 | .170 ± .045 | .110 ± .008 |
|  | 450 | .178 | .136 |
|  | 405 | .232 | .145 |
| Pd doped | 680 | .110 ± .017 | .043 ± .004 |
|  | 450 | .116 | .043 |
|  | 405 | .116 | .050 |
| Ru doped | 635 | .280 ± .021 | .080 ± .015 |
|  | 450 | .247 | .078 |
|  | 405 | .230 | .089 |
| Rh doped | 535 | .210 ± .027 | .100 ± .010 |
|  | 450 | .210 | .143 |
|  | 405 | .214 | .185 |

EXAMPLE 4

Figure 8:
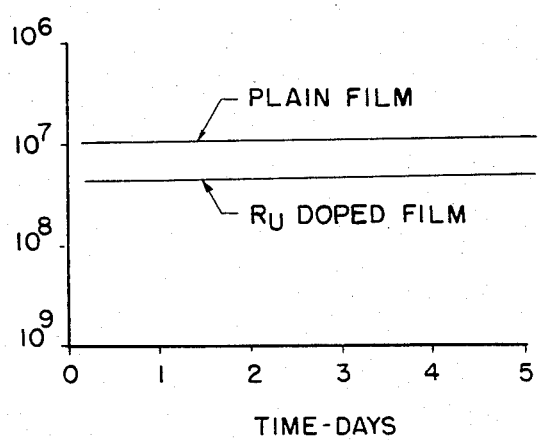
FIG. 8 is a graph of the transient dark current relationship for films exposed to methanol vapor.

Samples exposed to methanol vapor exhibited a decrease in film resistance for both plain and Ru-doped films. The surface film resistance decreased from one-half to one order of magnitude. With prolonged exposure, the conductivity change remained constant, as shown in FIG. 8. An important point to note was that films exposed to methanol vapor were regenerable in visible light. A weak form of chemisorption was suspected to have occurred. An alcohol radical most likely bonded to the surface and quickly reacted with generated electron holes.

In devising a viable sensor for gases, only the form of the functionality between the gas and conductivity needs to be known. A sensor can operate with the major amplification of changes in current response being amplified. This can be achieved by an integrated circuit, such as a RAM chip, or other suitable means.

The results obtained, to date, indicate that concentrations as low as 400 ppm are detectable for carbon monoxide. The illumination intensities needed for the photoresponse phenomena to occur are relatively low intensities, and can be achieved by a light-emitting diode (LED).

I claim:

1. A sensor for detecting the presence of an oxidizable gas contained in a mixture of gases, at ambient temperature comprising:

a semiconductive film sensor surface maintained at ambient temperature and having a resistivity of at least $10^4$ ohms/inch, the ability to chemisorb on its surface the oxidizable gas whose presence is to be detected, and a bandgap energy of from 0.5 eV to 5.0 eV, the surface exposed to the mixture of gases;

means for establishing an electrical potential across the sensor surface of the semiconductive film;

means for illuminating the film sensor surface with light energy having an intensity of 90 to 350 microwatts/$Cm^2$ at a frequency ranging from 380 to 680 nm to cause photodesorption/photoabsorption/photoreaction of the oxidizable gas in the gas mixture desired to be detected; and means for measuring the transient and steady state change in conductivity of the semiconductive film as a measure of the oxidizable gas being detected.

2. The sensor of claim 1 wherein the semiconductive film is one selected from the group consisting of metal oxides and metal oxides doped with a noble metal.

3. The sensor of claim 2 wherein the film has a resistivity equal to or greater than $10^7$ ohms/inch.

4. The sensor of claim 1 wherein the means for illuminating the film is pulsed intermittently with light of one or more wavelengths.

5. The sensor of claim 1 wherein the means for illuminating the semiconductive film is a light-emitting diode.

6. The sensor of claim 1 wherein the means for measuring the change in conductivity includes a solid-state integrated circuit to amplify the change in conductivity of the semiconductive film.

7. A sensor which operates at ambient temperatures for detecting the presence and amount of carbon monoxide contained in air, comprising:

a semiconductive film sensor surface maintained at ambient temperature and having a resistivity of at least $10^4$ ohms/inch, the ability to chemisorb carbon monoxide and a bandgap energy of 0.5 eV to 5.0 eV, the surface exposed to the air containing the carbon monoxide to be detected and measured;

means establishing an electrical potential across the surface of the semiconductive film;

means for intermittently illuminating the semiconductive film with visible light having a frequency ranging from 380–680 nm, an intensity of 90 to 350 microwatts/$cm^2$ to cause photodesorption of carbon monoxide reaction species and regeneration of the sensitivity of the semiconductive film and cuase a change in the conductivity of the semiconductive film; and means for measuring the transient and steady state change in conductivity of the semiconductive film as a measure of the concentration level of the carbon monoxide in the air.

8. A method of detecting the presence and/or amount of an oxidizable gas contained in a mixture of gases, comprising:

providing a semiconductive film sensor maintained at ambient temperature whose impedance is modulated by chemisorption of the gas molecules of the oxidizable gas in contact with the film surface, exposing the surface of the semiconductive film at ambient temperature to the mixture of gases;

establishing an electrical potential across the surface of the semiconductive film;

illuminating the semiconductive film surface with light of sufficient frequency and intensity to cause photodesorption of the oxidizable gas in the gas mixture being detected and/or measured; and measuring the change in conductivity of the semiconductive film as a measure of the presence and/or concentration of the oxidizable gas being chemisorbed.

9. The method of claim 8 wherein the semiconductive film is one selected from the group consisting of metal oxides and chalcogenides having bandgap energies anging from 0.5 eV to 5.0 eV and a resistivity of at least $10^4$ ohms/inch.

10. The method of claim 9 wherein the semiconductive film is doped with a noble metal.

11. The method of claim 8 wherein the semiconductive film is zinc oxide.

12. The method of claim 8 wherein the frequency and intensity of the light ranges from 90 to 350 microwatts/$Cm^2$ at a frequency ranging from 380 to 680 nm and wherein the semiconductive film contains zinc oxide.

13. The method of claim 8 wherein the oxidizable gas is carbon monoxide and the mixture of gases contains oxygen.

14. A method of quickly detecting the presence and/or concentration of carbon monoxide in a mixture of gases at ambient temperature by induced desorption/photoexitation of the absorbed gases on a semiconductive film surface, providing a semiconductive film surface maintained at ambient temperature selected from the group consisting of metal oxide and chalcogenides having bandgap energies ranging from 0.5 eV to 5.0 eV and a resistivity of at least $10^4$ ohms/inch, the semiconductive film modulated by chemisorption of the gas molecules of carbon monoxide in contact with the film surface, exposing the surface of the semiconductive film to the mixture of gases at ambient temperature, establishing electrical potential across the surface of the semiconductive film;

illuminating the semiconductive film surface with light having a frequency of from 380 to 680 nm and an intensity of from 90 to 350 microwatts/$Cm^2$ to cause photodesorption of carbon monoxide in the gas mixture; and measuring the change in conductivity of the semiconductive film as a measure of the presence and the concentration of the carbon monoxide in the mixture of gases.

15. The method of claim 14 wherein exposure of the semiconductive film to light is intermittent.

* * * * *